United States Patent [19]
Melody et al.

[11] Patent Number: 5,951,916
[45] Date of Patent: Sep. 14, 1999

[54] SOLUTIONS OF BUCKMINSTERFULLERENE ($C_{60}$) IN N-ETHYL-2-PYRROLIDONE (NEP)

[75] Inventors: Brian J. Melody, Greer; John T. Kinard, Simpsonville, both of S.C.

[73] Assignee: Kemet Electronics Corporation, Greenville, S.C.

[21] Appl. No.: 09/148,868

[22] Filed: Sep. 8, 1998

[51] Int. Cl.[6] .............................. C09K 31/02; B01F 1/00; C01B 31/00; C07C 7/00
[52] U.S. Cl. .............................. 252/364; 252/1; 585/833; 585/860; 585/862; 423/445 B
[58] Field of Search ........................ 252/1, 364; 585/833, 585/860, 862; 423/445 B

[56] References Cited

U.S. PATENT DOCUMENTS

| | | | |
|---|---|---|---|
| 5,114,477 | 5/1992 | Mort et al. | 55/485 |
| 5,281,406 | 1/1994 | Stalling et al. | 423/445 B |
| 5,310,532 | 5/1994 | Tour et al. | 423/445 B |
| 5,324,495 | 6/1994 | Gorun | 423/439 |
| 5,431,722 | 7/1995 | Yamashita et al. | 106/31.43 |
| 5,662,876 | 9/1997 | Tour et al. | 423/445 B |
| 5,698,174 | 12/1997 | Müller et al. | 423/445 B |

OTHER PUBLICATIONS

R. S. Ruoff et al., "Solubility of $C_{60}$ in a Variety of Solvents," *J. Phys. Chem.*, 1993, 97, 3379–3383.

W. A. Scrivens et al., "Potent Solvents for $C_{60}$ and their Utility for the Rapid Acquisition of $^{13}C$ NMR Data for Fullerenes," *J. Chem. Soc., Chem. Commun.*, 1993, 1207–1209.

Journal of Electrochemical Society. vol. 139, No. 4; Entry 659 FUL "Solubility of Buckminsterfullerene, $C_{60}$, in Water and Some Polar Organic Solvents by Cyclodextrin Inclusion Chemistry" W. Kutner et al, Apr. 1992.

Journal of Chemical Society "$C_{60}$ Embedded in γ–Cyclodextrin: A Water Soluble Fullerene" Thomas Andersson et al, 1992 (No Month Available).

Journal of Organic Chemistry. vol. 57; pp. 6077–6079. "Solubility of $C_{60}$ in Organic Solvents" N. Sivaraman et al, 1992( No Month Available).

Chemical Physics Letters "Extraction of Giant Fullerene Molecules, and Their Subsequent Solvation in Low Boiling Point Solvents" C. Smart et al, Sep. 1991.

*Primary Examiner*—Cynthia Harris Kelly
*Assistant Examiner*—LaToya Cross
*Attorney, Agent, or Firm*—Banner & Witcoff, Ltd.

[57] ABSTRACT

A solution comprising a polar solvent and $C_{60}$ in which the solubility of $C_{60}$ is at least 2 mg/ml of solvent. The polar solvent has a low toxicity, high boiling point, high thermal and electrochemical stability, low viscosity, low freezing point, a high dielectric constant, and is relatively inexpensive. Preferably the polar solvent is N-ethyl-2-pyrrolidone.

5 Claims, No Drawings

SOLUTIONS OF BUCKMINSTERFULLERENE ($C_{60}$) IN N-ETHYL-2-PYRROLIDONE (NEP)

FIELD OF THE INVENTION

The present invention is directed to solutions of buckminsterfullerene ($C_{60}$) and the polar solvent N-ethyl-2-pyrrolidone which are useful for the deposition of $C_{60}$ via evaporation of the solvent, for the preparation of electron transfer complexes of $C_{60}$, and for the direct electrochemical reaction of unsubstituted $C_{60}$.

BACKGROUND OF THE INVENTION

Since the announcement of the discovery of $C_{60}$, buckminsterfullerene, in 1985 ("$C_{60}$: Buckminsterfullerene," H. W. Kroto, J. R. Heath. S. C. O'Brien, R. F. Curl, and R. E. Smalley, Nature, Vol. 318, 1985, pp 162–163) and the announcement of the discovery of a method of producing macroscopic quantities of $C_{60}$ in 1990 ("Solid $C_{60}$: A New Form of Carbon," W. Kratschmer, Lowell D. Lamb, K. Fostiropoulos, and Daniel R. Huffinan, Nature, Vol. 347, 1990, pp 354–358), a substantial amount of research has been conducted on this recently recognized form of carbon, specifically to finding a polar solvent that has a high boiling point, low toxicity, a high dielectric constant, high thermal and electrochemical stability, low viscosity and freezing point, and is relatively inexpensive in which $C_{60}$ is highly soluble. In the above cited paper, Kratschmer, et al., reported that buckminsterfullerene is soluble in benzene, giving a "wine red to brown liquid" (pg. 354). The solubility of $C_{60}$ in benzene was exploited by authors for the extraction of $C_{60}$ from condensed soot produced in the electric arc between carbon rods and for the deposition of the pure material from benzene solutions. However, benzene does not meet the profile of a desired solvent due to it being non-polar and a suspected carcinogen.

In 1993, Ruoff, et al., reported on the solubility of $C_{60}$ in a wide variety of solvents ("Solubility of $C_{60}$ in a Variety of Solvents," R. S. Ruoff, Doris S. Tac, R. Malhotra, and D. C. Lorents, Journal of the American Chemical Society, Vol. 97, No. 13, 1993, 3319–3323). These authors report that $C_{60}$ is soluble (up to approximately 50 mg/ml) in benzene and naphthalene derivatives, sparingly soluble in substituted alkanes (up to approximately 1 mg/ml), and insoluble in polar solvents (less than 0.003 mg/ml). These authors concluded that, while solubility trends are predictable for various classes of solvents, solubility in any particular solvent must be individually tested. This conclusion was supported by the exceptionally high solubility (0.89 mg/ml) of $C_{60}$ in N-methyl-2-pyrrolidone (NWP) considering the authors statement regarding the insolubility of $C_{60}$ in polar solvents and the high polarity of NMP (dielectric constant=32.2). The preparation (i.e., solvent extraction of $C_{60}$ from condensed carbon-arc soot) and use (i.e., electrochemical applications) of $C_{60}$ are inhibited to some degree by the very low solubility of $C_{60}$ in low-toxicity solvents. The solvents in which $C_{60}$ are most soluble, the chlorinated aromatics (benzene, naphthalene, etc.) are suspected carcinogens. Although, the electrochemistry of $C_{60}$ has been determined through the preparation of polar solvent-soluble derivatives or through the use of mixed solvents/supporting electrolytes such as those described by Muller and Heinze ("Direct Electrochemical Detection of $C_{60}$ in Solution by Steady-State Voltammetry at Microelectrodes," R. Muller and J. Heinze, Journal of the Electrochemical Society, Vol. 145, No. 4, 1998, pp 1227–1232), the potential electrochemical applications broadly expand if a single polar solvent is found. None of the preceding documents disclose a polar solvent that meets the aforementioned criteria. In fact, one of the above documents teaches that a polar solvent generally will not have a high solubility for $C_{60}$ regardless of the solvent's other properties.

SUMMARY OF THE INVENTION

The present invention is directed to a solution comprising: (a) a polar solvent and (b) $C_{60}$, wherein the solubility of $C_{60}$ in the polar solvent is at least 2 mg $C_{60}$ per ml of solvent. More specifically, the present invention is directed to solutions of buckminsterfullerene ($C_{60}$) dissolved in N-ethyl-2-pyrrolidone (NEP), NEP is a polar solvent that meets all of the aforementioned criteria and has a surprisingly high solvency for $C_{60}$. The use of NEP as a solvent increases the amount of $C_{60}$ prepared via evaporation of the solvent (after extraction of the solvent from soot or from solutions prepared by contact between $C_{60}$ and NEP). The $C_{60}$/NEP solutions can also be used in the preparation of electron transfer complexes of $C_{60}$ (e.g., $C_{60}$ complexes with TCNQ), and for direct electrochemical reactions of unsubstituted $C_{60}$.

DETAILED DESCRIPTION OF THE PREFERRED EMBODIMENTS

The present invention is directed to a polar solvent for $C_{60}$ in which $C_{60}$ has a surprisingly high solubility and to the solutions of $C_{60}$ in this polar solvent. Particularly, the present invention is directed to a solution comprising: (a) a polar solvent and (b) $C_{60}$, wherein the solubility of $C_{60}$ in the polar solvent is at least 2 mg $C_{60}$ per ml of solvent, preferably at least 3 mg $C_{60}$ per ml of solvent, and more preferably at least 5 mg $C_{60}$ per ml of solvent.

The polar solvent should have a low toxicity, a high boiling point and dielectric constant, high thermal and electrochemical stability, low viscosity, a low freezing point, and be relatively inexpensive. A polar solvent that meets the aforementioned criteria and in which $C_{60}$ has a surprisingly high solubility is NEP-N-ethyl-2-pyrrolidone. The solutions are formed by dissolving $C_{60}$ in NEP.

NEP is similar to N-methyl-2-pyrrolidone in many properties. The boiling point of NEP is in excess of 200° C. NEP has a high dielectric constant (28.2), a low viscosity, below 10 c.p.s., e.g. similar to water, and is not presently considered by industry or the federal government as a hazardous chemical.

Amnine salt solutions in 75% NEP/25% cosolvent are known as electrolytic capacitor electrolytes and are very thermally and electrically stable as indicated by the examples in U.S. Pat. No. 4,812,951. The very low freezing point of NEP (below –70° C.) suggests that substantially less intermolecular hydrogen bonding is present in NEP than NMP (freezing point=–26° C.), giving NEP a pseudo aromatic nature. It is believed that this "pseudo-aromatic" nature of NEP facilitates dissolution of $C_{60}$.

It was discovered that the solubility of $C_{60}$ in NEP exceeded the solubility of $C_{60}$ in NMP (0.89 mg $C_{60}$/ml NMP). Particularly, NEP has a solubility of at least 5 mg $C_{60}$/ml NEP. This is a surprising increase of over 500% compared to the solubility of $C_{60}$ in NMP. The solutions of $C_{60}$ in NEP are the wine-red to brown color associated with $C_{60}$ solutions in the toxic aromatic solvents.

The use of NEP as a solvent for $C_{60}$ facilitates the preparation of solutions approximately an order of magnitude more concentrated than NMP and over 3 orders of magnitude more concentrated than traditional polar organic solvents, e.g. water, alcohols, etc.

By dissolving $C_{60}$ in NEP, greater amounts of $C_{60}$ may be obtained from low toxicity/high flash point extraction separation of $C_{60}$ from condensed carbon soots. Generally, the soot and NEP are stirred together. The soot is allowed lo settle and the red solution of $C_{60}$ is decanted.

The solutions may also be used in the preparation of $C_{60}$ films via solvent evaporation. $C_{60}$ is dissolved in NEP to form a solution. The solution its applied to a surface and then the NEP is evaporated to leave a film. Heat is desirable to advance the evaporation. Additionally, the solutions may be used in the preparation of electrically bistable films (for switches, etc.) consisting of $C_{60}$ complexes, such as the $C_{60}$/TCNQ complexes described by Gao, et. al. ("Fullerene-Tetracyanoquinodimethane Thin Film and Novel Electrical Bistablity," H. J. Gao, Z. Q. Xue, Q. D. Wu, and S. J. Pang, Journal of Material Research, Vol. 11, No. 16, 1996, 1996, pp 2192–2194), via a solution route. The $C_{60}$/TCNQ complex is dissolved in NEP to form a solution. The solution is applied to a surface and NEP is allowed to evaporate. The solutions may also be used in electrochemical reactions/ syntheses involving dissolved $C_{60}$ without requiring prior derivitization and minimizing solvent decomposition. Various polar solvents-soluble species, organic or inorganic or both, may be dissolved in NEP-$C_{60}$ solutions for electrochemical reaction as graphite or platinum electrodes.

EXAMPLE 5 mg/g $C_{60}$ in NEP was prepared by allowing the $C_{60}$ to stand in contact with the NEP for 72 hours without heating or stirring.

What is claimed:

1. A solution comprising: (a) a polar solvent and (b) $C_{60}$ wherein the solubility of $C_{60}$ in the polar solvent is at least 2 mg $C_{60}$ per ml of solvent.

2. The solution according to claim 1, wherein N-ethyl-2-pyrrolidone has a boiling point of at least 200° C.

3. The solution according to claim 1, wherein N-ethyl-2-pyrrolidone has a dielectric constant of at least 28.2.

4. The solution according to claim 1, wherein N-ethyl-2-pyrrolidone has a viscosity below 10 cps.

5. The solution according to claim 1 wherein the solubility of $C_{60}$ in said N-ethyl-2-pyrrolidone is at least 5 mg $C_{60}$ per ml of solvent.

* * * * *

UNITED STATES PATENT AND TRADEMARK OFFICE
CERTIFICATE OF CORRECTION

PATENT NO. : 5,951,916
DATED : September 14, 1999
INVENTOR(S) : Brian J. MELODY, et al.

It is certified that errors appear in the above-identified patent and that said Letters Patent is hereby corrected as shown below:

In Claim 1, column 4, line 12, after the word "solvent", the phrase --of N-ethyl-2-pyrrolidone-- has been inserted.

In Claim 5, column 4, line 22, the word "said" has been deleted.

Signed and Sealed this

Twenty-seventh Day of February, 2001

Attest:

NICHOLAS P. GODICI

Attesting Officer

Acting Director of the United States Patent and Trademark Office